United States Patent [19]
Klabunde et al.

[11] Patent Number: 6,087,294
[45] Date of Patent: Jul. 11, 2000

[54] DISPERSION AND STABILIZATION OF REACTIVE ATOMS ON THE SURFACE OF METAL OXIDES

[75] Inventors: Kenneth J. Klabunde; Naijian Sun, both of Manhattan, Kans.

[73] Assignee: Kansas State University Research Foundation, Manhattan, Kans.

[21] Appl. No.: 09/133,301

[22] Filed: Aug. 12, 1998

[51] Int. Cl.$^7$ ............................... B01J 27/06; B01J 23/04
[52] U.S. Cl. .................... 502/224; 502/226; 502/227; 502/229; 502/231; 502/324; 502/325; 502/328; 502/329; 502/330; 502/332; 502/336; 502/337; 502/338; 502/344; 502/340
[58] Field of Search ...................... 502/224, 226, 502/227, 229, 231, 324, 325, 328, 330, 332, 336, 337, 338, 344, 340

[56] References Cited

U.S. PATENT DOCUMENTS

| | | | |
|---|---|---|---|
| 4,672,145 | 6/1987 | Kolts et al. ............................... | 585/658 |
| 4,728,636 | 3/1988 | Sofranko ................................. | 502/324 |
| 4,895,823 | 1/1990 | Kolts et al. ............................. | 502/226 |
| 4,997,802 | 3/1991 | Matsuura et al. ....................... | 502/303 |
| 5,071,815 | 12/1991 | Wallace et al. ......................... | 502/302 |

OTHER PUBLICATIONS

Tanabe, K., Misono,M.; Ono, Y. and Hattori, H. "New Solid Acids and Bases", Elsevier, Amsterdam, p. 38, 213, 2131 (1989), no month available.

Matsuhashi, H. and Arata, K. J. Phys. Chem., 99, 11178 (1995), no month available.

Haag, W.O. and Pines, H. J. Am. Chem. Soc., 82, 387 (1960), no month available.

Matsuda, t., Tanabe, J., Hayashi, N., Sasaki, Y. Miura, H. and Sugiyama, K. Bull. Chem. Soc. Jpn., 55, 990–994 (1982), no month available.

*Primary Examiner*—Elizabeth D. Wood
*Attorney, Agent, or Firm*—Hovey, Williams, Timmons & Collins

[57] ABSTRACT

Particulate metal oxide compositions having reactive atoms stabilized on particulate surfaces and methods for reacting the compositions with saturated and unsaturated species are provided. The preferred particulate metal oxides of the compositions are nanocrystalline MgO and CaO with an average crystallite size of up to about 20 nm. The preferred reactive atoms of the compositions are atoms of the halogens and Group IA metals. In one embodiment, chlorine atoms are stabilized on the surface of nanocrystalline MgO thus forming a composition which is capable of halogenating compounds, both saturated and unsaturated, in the absence of UV light and elevated reaction temperatures.

51 Claims, 9 Drawing Sheets

○ $O^{2-}$  ● $Mg^{2+}$  ⊕ $K^+$  ⊖ ELECTRON

DISPERSION AND STABILIZATION OF REACTIVE ATOMS ON THE SURFACE OF METAL OXIDES

BACKGROUND OF THE INVENTION

1. Field of the Invention

The present invention is broadly concerned with particulate metal oxide compositions having stabilized on the particulate surface reactive atoms selected from the group consisting of atoms of the halogens and Group IA metals. Preferred particulate metal oxides include nanocrystalline MgO and CaO, with average crystallite sizes of up to about 20 nm. In one embodiment, potassium atoms are stabilized on the surface of nanocrystalline MgO at a loading of from about 10–40% by weight potassium based on the total weight of the K/MgO composite, thus forming superbases useful for isomerizing and alkylating unsaturated species. In another embodiment, chlorine atoms are stabilized on the surface of nanocrystalline MgO thus forming a composition which is capable of halogenating compounds in the absence of UV light and elevated temperatures, as well as providing a non-water utilizing source of chlorine for bleaching purposes.

2. Description of the Prior Art

Nanocrystalline metal oxides having an average crystallite size of up to about 20 nm are known to possess surface reactivities and adsorptive powers which are considerably higher than typically available metal oxide samples. It is believed that the enhanced surface reactivities of these nanocrystalline metal oxides are due to morphological features of the small crystallites, such as the higher population of reactive surface sites at edges and corners, and at sites with ion vacancies. The small sizes and unusual shapes of the crystallites provide high ratios of edge/corner ions to total surface ions. The presence of these edge/corner sites and other reactive defect sites (such as vacancies) allow these materials to possess surprisingly high surface concentrations of reactive surface ions. For example, an edge or corner $O^{2-}$ anion is coordinatively unsaturated and is "seeking" Lewis acids to help stabilize and delocalize its negative charge. Conversely, an $Mg^{2+}$ ion on an edge or corner site is "seeking" Lewis bases to stabilize and delocalize its positive charge. Therefore, these coordinatively unsaturated $O^{2-}$ and $Mg^{2+}$ readily accept incoming reagents with Lewis base or Lewis acid characteristics.

Solid superbases (as used hereinafter, bases which are strong enough to extract a proton from toluene) are generally created when metal oxides are treated with alkali metals. These materials are capable of acting as catalysts for the isomerization of alkenes at room temperature. However, they are only capable of alkylation reactions at high reaction temperatures (i.e., 150° C. or greater), and even then only for certain types of alkylations. These drawbacks result from the inability to achieve sufficiently high loadings of the alkali metal in the form of dissociated metal ions and electrons on the metal oxide surfaces. That is, in order to create superbases with enhanced alkylation abilities, higher and heretofore unobtainable alkali metal loadings are required.

Halogens exist as stable diatomic molecules unless contacted with an oxidizable compound. To halogenate a molecule, it is first necessary to dissociate the diatomic molecule into halogen atoms which are reactive. For example, if $Cl_2$ is added to methane, no reaction will occur because the diatomic chlorine is very stable and non-reactive. However, if UV light is added, or if the reaction is carried out at a temperature of about 300° C., the $Cl_2$ will dissociate into highly reactive chlorine atoms, thus chlorinating the methane or re-forming $Cl_2$ if there is inadequate methane available for reaction. There are no methods in the prior art by which halogens can be stabilized in the form of reactive atoms, absent use of UV light or high reaction temperatures.

There is a need for superbase compounds with increased surface base site concentrations as well as stronger base sites which are capable of alkene isomerization and dimerizations, including propylene-ethylene conversion to pentenes and heptenes. Furthermore, there is a need in the art for processes by which halogens can be stabilized on metal oxide particles as reactive atoms without the need for UV light or high temperatures.

SUMMARY OF THE INVENTION

The present invention overcomes these problems and provides compositions comprising particulate metal oxides having stabilized reactive atoms on the surfaces thereof, as well as methods for isomerizing, alkylating, and halogenating unsaturated species (e.g. alkenes) as well as halogenating alkanes using such compositions.

In more detail, the compositions of the invention comprise metal oxide particles having oxygen ion moieties on their surfaces with reactive atoms interacted or chemisorbed with those surface oxygen ions. Preferably, the metal oxide particles are taken from the group consisting of oxides of Mg, Ca, Ti, Zr, Fe, V, Mn, Fe, Ni, Cu, Al, Zn, or mixtures thereof, with MgO and CaO being particularly preferred. While conventionally prepared metal oxide particles can be used to form the compositions, the preferred particles are nanoparticles prepared by aerogel techniques from Utamapanya et al., *Chem. Mater.*, 3:175–181 (1991). The metal oxide particles should advantageously have an average crystallite size of up to about 20 nm, more preferably from about 3 to 9 nm, and most preferably about 4 nm. Furthermore, the particles should have a BET multi-point surface area of at least about 15 $m^2/g$, preferably at least about 200 $m^2/g$, and more preferably at least about 500 $m^2/g$.

Preferably, the reactive atoms of the compositions are selected from the group consisting of atoms of halogens and Group IA metals. When stabilizing a Group IA metal atom, the atom loading on the metal oxide should be from about 5% to about 40% by weight, preferably from about 10% to about 15% by weight, and most preferably about 12% by weight, based upon the weight of the atom-loaded metal oxide taken as 100%. The atom loading on the metal oxide can also be expressed as a concentration of atoms per unit of surface area of the metal oxide, i.e., at least about 2 atoms per $nm^2$ of metal oxide surface area, preferably about 3–8 atoms per $nm^2$ of metal oxide surface area, and more preferably about 4–5 atoms per $nm^2$. The preferred Group IA metal utilized in compositions of the invention is potassium.

The metal oxide-atom adducts of the invention exhibit certain characteristics of classical oxygen-atom bonding, but probably cannot properly be characterized in that way. Rather, the adducts exhibit a type of hybrid weak bonding or chemisorption between the metal oxide $O^{2-}$ reactive sites and the stabilized atoms. Depending upon ambient pressure conditions, the adducts in a closed system reach an equilibrium condition where some of the surface-bound atoms migrate from the oxide and atoms in the gaseous phase reattach to the oxide surface sites. In the case of chlorine-containing adducts for example, small amounts of $Cl_2$ gas can be observed in a closed system which indicates that chlorine atoms migrate from the oxide surface and dimerize, while ambient $Cl_2$ molecules react to split and attach the chlorine atoms to open reactive sites, to establish an equilibrium condition.

The compositions are formed by heating a quantity of particulate metal oxide particles to a temperature of at least about 200° C., preferably at least about 300° C., and more preferably to a level of from about 450 to about 500° C. Heating the metal oxide particles to these temperatures removes water from the particles so that the final compositions of the invention have a surface hydroxyl concentration of less than about 5 hydroxyl groups per square nanometer of metal oxide surface area, and preferably less than about 4 hydroxyl groups per square nanometer of metal oxide surface area. The particles are preferably allowed to cool to room temperature. The particles are then contacted with a source of reactive atoms, e.g., a diatomic molecule which dissociates into reactive atoms under the proper reaction conditions. The reactive atoms interact with the metal oxide surface oxygen ions, thus stabilizing the atoms on the oxide surface. As used hereinafter, the terms "stabilized" and "stable" mean that, when the metal oxide-atom adducts are heated to a temperature of about 100° C., less than about 10% of the total weight loss of the adduct is attributable to the reactive atoms desorbing.

The metal oxide-atom adducts of the invention can also be formed into pellets for situations where nanoscale size particles are impractical. These pellets are formed by agglomerating the finely divided metal oxide-atom adducts by any suitable process, e.g., pressing at a pressure of from about 50 psi to about 6,000 psi, more preferably from about 500 psi to about 5000 psi and most preferably to about 2000 psi. While these pressures are typically applied to the metal oxide-atom adducts by way of an automatic or hydraulic press, the pellets can be formed by any pressure-applying means. Furthermore, a binder or filler can be mixed with the metal oxide-atom adducts, and/or the pellets can be formed by pressing the mixture by hand. Agglomerating or agglomerated as used hereinafter thus includes all of the known processes for this purpose such as centrifugation techniques or pressing together of the metal oxide-atom adduct particles.

The halogenated metal oxide compositions of this invention can be utilized to halogenate unsaturated species (such as alkenes) as well as saturated species (such as alkanes). This is accomplished by contacting the composition with a target compound at a very broad temperature range of from about −80 to about 240° C., but preferably the contacting temperature is less than about 25° C., more preferably less than about 0° C., and most preferably less than about −23° C. If the metal oxide-stabilized atom composition used is Cl/CP—CaO or Cl/AP—MgO, the contacting step is carried out at a temperature of less than about −42° C. and preferably less than about −78° C. Advantageously, this invention provides compositions and methods to halogenate (and particularly chlorinate) saturated compounds in the absence of UV light and without high reaction temperatures characteristic of the prior art. Furthermore, the chlorinated metal oxide compositions of the invention can be utilized as a source of chlorine for bleaching purposes without requiring the use of water.

The superbase compositions of this invention are useful for isomerizing and alkylating alkenes and other unsaturated species. Alkenes are isomerized by contacting the superbase compositions with an alkene, preferably under an alkene pressure of about 80–120 psi. The superbase compositions and methods for isomerizing alkenes is particularly useful for converting DMB (2,3-dimethyl-1-butene) to tetramethylethylene, and 1-pentene to trans- or cis-2-pentene.

Alkenes or other species are alkylated by contacting a superbase composition hereof with a first alkene (such as propylene) under an alkene pressure of about 80–120 psi. The resulting product is then contacted with a second alkene (such as ethylene), preferably at a second alkene pressure of about 80–120 psi. The second alkene is thus alkylated by the first alkene.

DETAILED DESCRIPTION OF THE PREFERRED EMBODIMENTS

Figure 1:
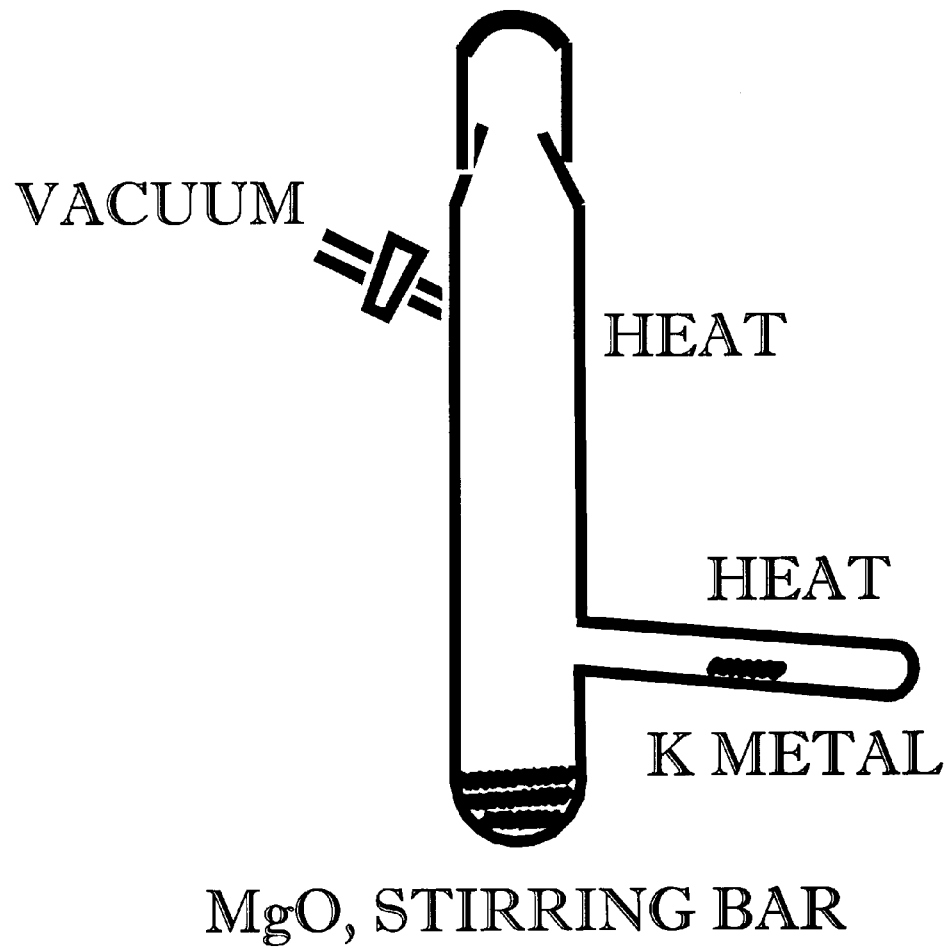
FIG. 1 illustrates the experimental set-up utilized in preparing a K/MgO adduct of the invention in a Schlenk tube.

The following examples set forth preferred methods in accordance with the invention. It is to be understood, however, that these examples are provided by way of illustration and nothing therein should be taken as a limitation upon the overall scope of the invention. In these examples, "AP—MgO" and "AP—CaO" refer to the respective aerogel (or autoclave) prepared oxides. "CP—MgO" and "CP—CaO" refer to the respective oxides produced by conventional techniques.

EXAMPLE 1A

Determination of Surface Areas

The Brunauer-Emmett-Teller (BET) multi-point gas absorption method was employed using $N_2$ adsorption at liquid $N_2$ temperature to measure the surface area/unit mass. The BET surface area measurement techniques are described in *Introduction to Powder Surface Area*, Lowell, S., John Wiley & Sons: New York (1979), incorporated by reference herein.

EXAMPLE 1B

Preparation of MgO Samples

1. AP—MgO

Highly divided nanocrystalline $Mg(OH)_2$ samples were prepared by the autoclave treatment described by Utamapanya et al., *Chem. Mater.*, 3:175–181 (1991), incorporated by reference herein. In this procedure, 10% by weight magnesium methoxide in methanol solution was prepared and 83% by weight toluene solvent was added. The solution was then hydrolyzed by addition of 0.75% by weight water dropwise while the solution was stirred and covered with aluminum foil to avoid evaporation. To insure completion of the reaction, the mixture was stirred overnight. This produced a gel which was treated in an autoclave using a glass lined 600 ml capacity Parr miniature reactor. The gel solution was placed within the reactor and flushed for 10 minutes with nitrogen gas, whereupon the reactor was closed and pressurized to 100 psi using the nitrogen gas. The reactor was then heated up to 265° C. over a 4 hour period at a heating rate of 1° C./min. The temperature was then allowed to equilibrate at 265° C. for 10 minutes (final reactor pressure was about 700 psi). At this point, the reactor was vented to release the pressure and vent the solvent. Finally, the reactor was flushed with nitrogen gas for 10 minutes. The $Mg(OH)_2$ particles were then thermally converted to MgO. This was accomplished by heating the $Mg(OH)_2$ under dynamic vacuum ($10^{-2}$ Torr) conditions at an ascending temperature rate to a maximum temperature of 500° C. which was held for 6 hours resulting in AP—MgO with a BET surface area of 300–600 $m^2/g$ and an average crystallite size of 4nm. Further details about the MgO preparation can be found in PCT Publication WO 95/27679, also incorporated by reference herein.

2. CP—MgO

CP—MgO samples were prepared by boiling commercially available MgO (Aldrich Chemical Company) for five hours, followed by drying of the sample at 120° C. for five hours. The sample was then dehydrated under vacuum at 500° C. resulting in CP—MgO with a BET surface area of 130–200 $m^2/g$ and an average crystallite size of 8.8 nm.

EXAMPLE 2

Materials and Methods

1. Preparation of K/AP—MgO and K/CP—MgO Super Base Catalyst

An inert atmosphere Schlenk tube bearing a side arm (see FIG. 1) was charged with 1.0 g of AP—MgO or CP—MgO prepared as described in Example 1. Freshly cut potassium was placed in the side tube. The system was evacuated, and the side tube was heated to approximately 300° C. for 30 minutes. All of the potassium metal was either evaporated or adsorbed by the MgO while the MgO was stirred magnetically.

2. Procedures for Isomerization of Alkenes

DMB (2,3-dimethyl-1-butene) or 1-pentene was dried over 4 Å molecular sieves at room temperature. The K/MgO catalyst prepared in Part 1 of this example (either K/AP—MgO or K/CP—MgO) was added to an argon filled flask. Two ml of DMB (0.0162 mole) or 3 ml of 1-pentene (0.0275 mole) were injected onto the catalyst, and the resulting mixture was stirred for 30 minutes at room temperature.

3. Procedure for Alkylation of Alkenes

A Hastaloy-C 250 ml autoclave was placed in an inert atmosphere box, and 0.3 g of K/MgO (either K/AP—MgO or K/CP—MgO) catalyst was placed in the autoclave. The autoclave was then removed from the inert atmosphere box and evacuated. A first alkene gas was allowed to expand into the autoclave to approximately 100 psi and was condensed by placing the autoclave in a dry-ice, acetone bath. Next, a second alkene gas was allowed to expand into the autoclave to a pressure of approximately 100 psi. The moles of alkenes were derived using the pressure-volume relationship. The sealed autoclave was heated to 180° C. or 210° C. for approximately two hours while stirring. Next, the volatile reaction products were collected in cold traps (−78° C. and −196° C.) under vacuum.

EXAMPLE 3

Attempted Isomerization of Alkenes by AP—MgO and CP—MgO

Both AP—MgO and CP—MgO samples without potassium were exposed to DMB following the procedure described in Part 2 of Example 2. The resulting product was analyzed by gas chromatography. The test was repeated with 1-pentene in place of DMB. No isomerization of the alkenes took place in either instance. These results indicate that particulate MgO does not possess base sites strong enough to remove allylic protons from 1-pentene or DMB.

EXAMPLE 4

Isomerization of Alkenes By Potassium-Loaded Metal Oxides

1. DMB

Figure 2:
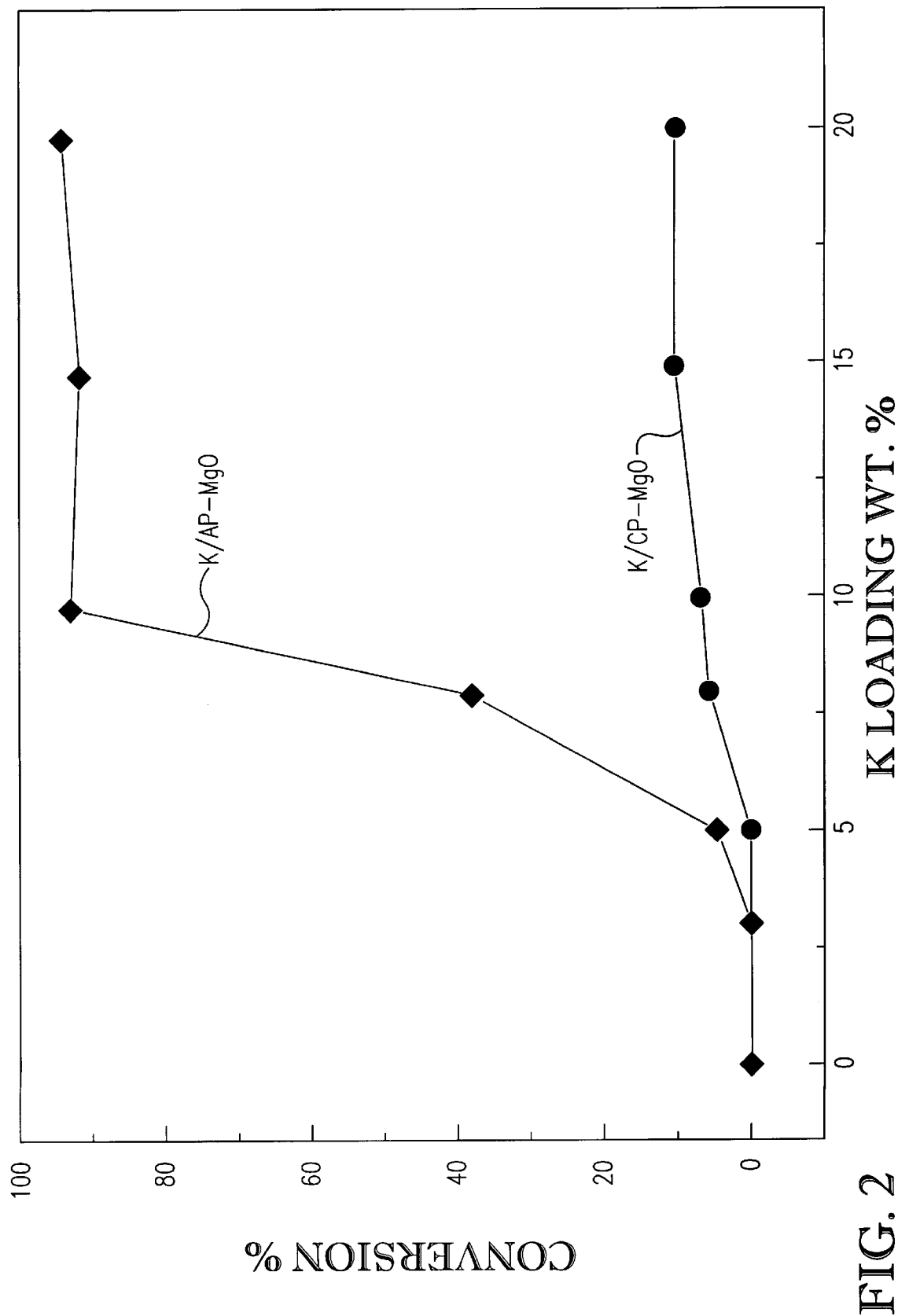
FIG. 2 is a graph depicting the extent of isomerization of DMB by K/AP—MgO compared to the extent of isomerization of DMB by K/CP—MgO.

AP—MgO and CP—MgO (0.1 g) were loaded with potassium vapor following the procedures described in Part 1 of Example 2. The loading of potassium on the metal oxide surfaces ranged from 1 to 20% by mass. Two ml of liquid DMB was allowed to contact each sample (AP—MgO or CP—MgO at various potassium loadings) at room temperature for 30 minutes. The resulting material was analyzed by gas chromatography in order to determine the percent conversion of DMB to tetramethylethylene. These results are set forth in FIG. 2 and illustrate that the activity of the K/AP—MgO is much higher than the activity of the K/CP—MgO. At loadings of 10%, 15%, and 20% of potassium on AP—MgO, there was nearly a 100% conversion of DMB to tetramethylethylene. For similar potassium loadings on CP—MgO there was only about 10% conversion of DMB to tetramethylethylene. The BET surface area of K/AP—MgO is 128 $m^2/g$ while the BET surface area of K/CP—MgO is 83 $m^2/g$. Such a substantial difference in percent conversion of DMB to tetramethylethylene cannot be attributed solely to the difference in surface areas of K/AP—MgO and K/CP—MgO. Rather, these results indicate that this high conversion with K/AP—MgO is in part due to the edge reactive sites available on the AP—MgO for potassium interaction.

2. 1-Pentene

Figure 3:
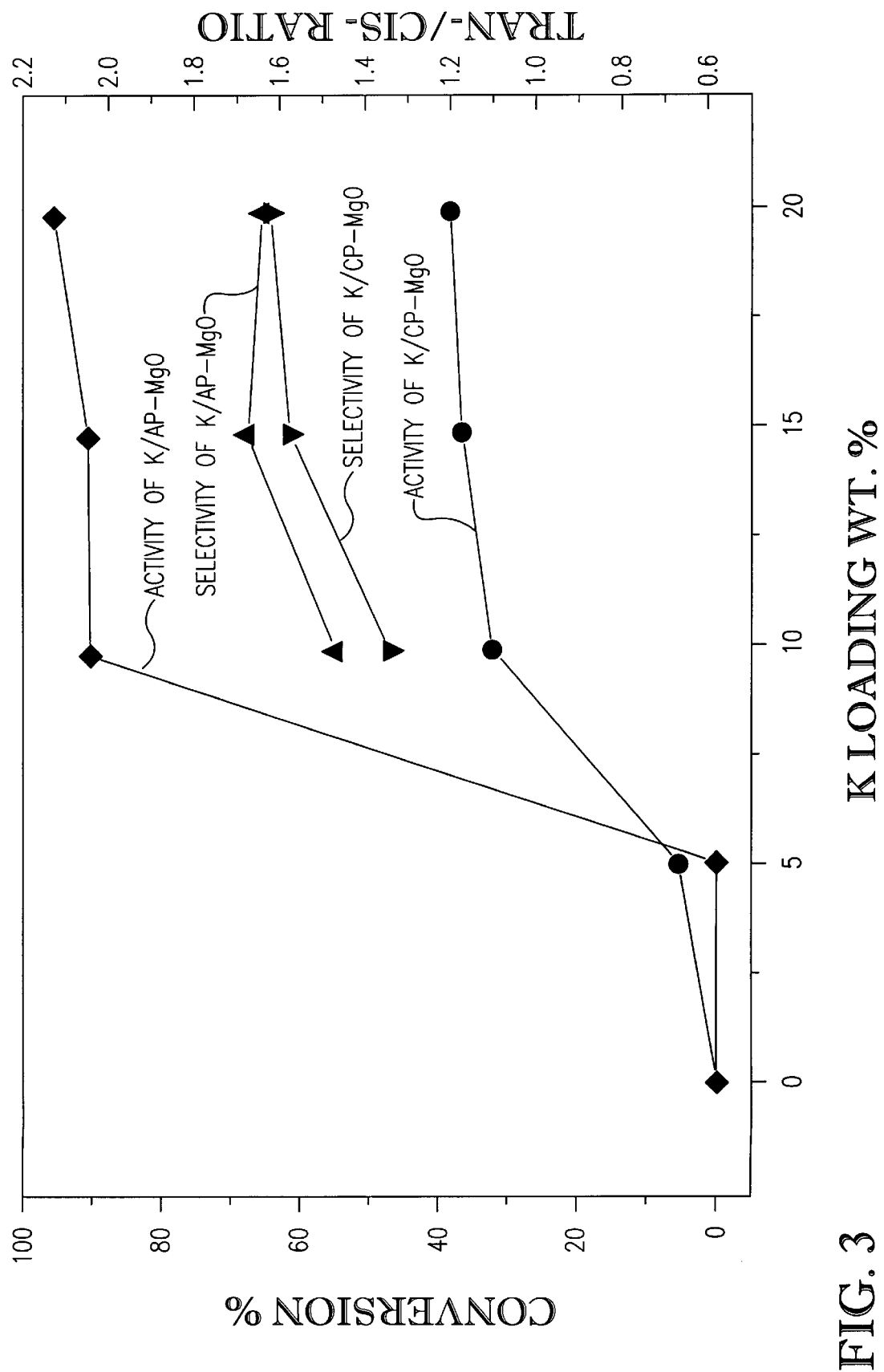
FIG. 3 is a graph illustrating the effect of potassium loading on AP—MgO and CP—MgO samples on the extent of isomerization of 1-pentene.

This experiment was repeated using 1-pentene in place of DMB. The results are set forth in FIG. 3 and indicate that, at a 10% or greater loading of potassium on AP—MgO, there was a 90% conversion of 1-pentene to trans/cis-2-pentene. At the same potassium loadings on CP—MgO there was a 38–40% conversion of 1-pentene to trans/cis-2-pentene. There was almost no difference in the selectivities of the K/AP—MgO and the K/CP—MgO towards forming the cis or trans isomer.

EXAMPLE 5

Alkylation of Ethylene and Propylene by Toluene and AP—MgO

Figure 4:
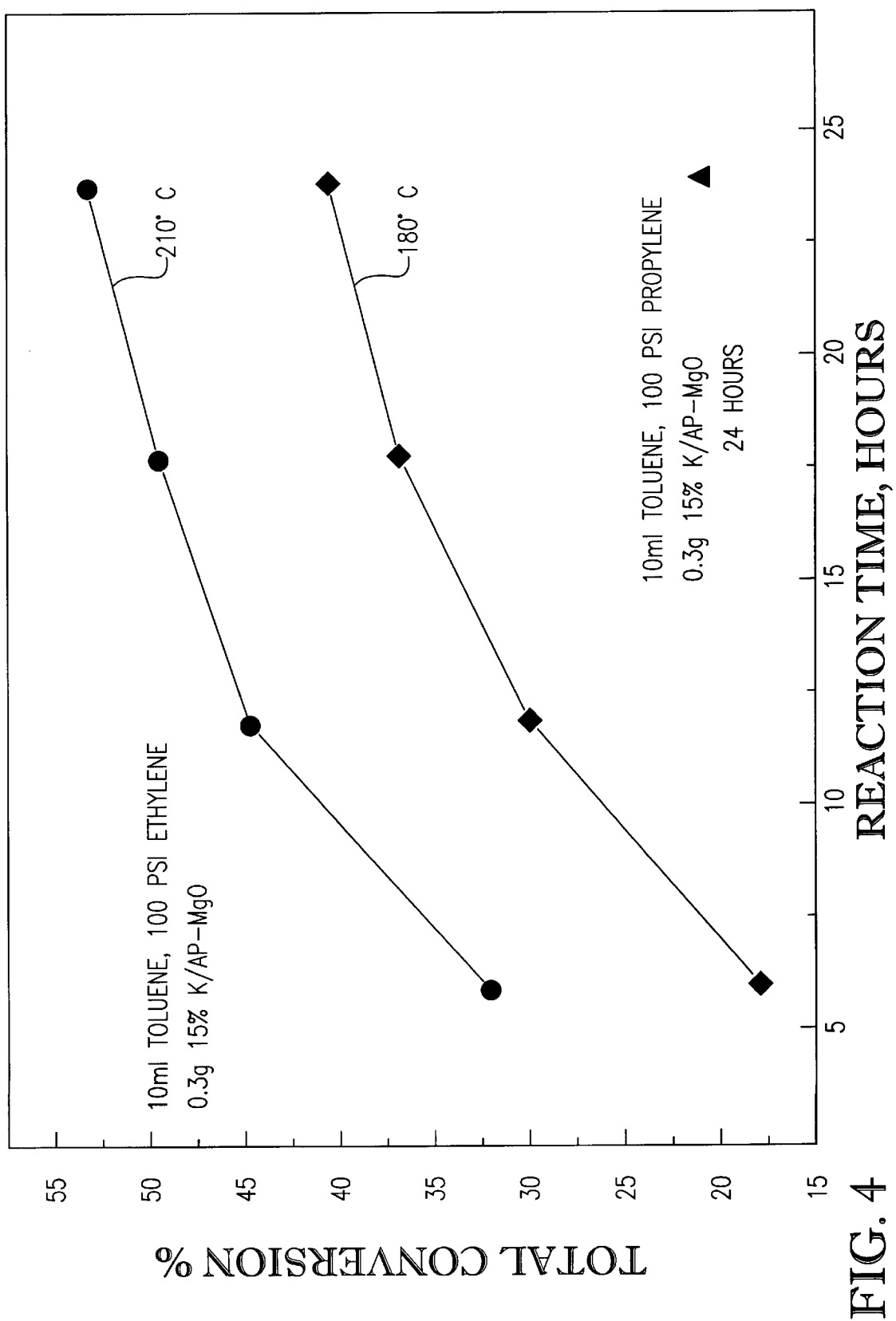
FIG. 4 is a graph comparing the extent of alkylation of propylene by toluene with the extent of alkylation of ethylene by toluene utilizing a 15% by weight potassium loading on AP—MgO based on the total weight of AP—MgO sample.

A Hastaloy-C 250 ml autoclave was placed in an inert atmosphere box, and 0.3 g of AP—MgO with a 15% by weight loading of potassium (based on the total weight of the AP—MgO sample) and 10 ml of toluene were placed in the autoclave. The autoclave was then removed from the inert atmosphere box and evacuated. Ethylene gas was allowed to expand into the autoclave to approximately 100 psi. The ethylene was condensed by placing the autoclave in a dry-ice, acetone bath. The moles of ethylene were derived by the pressure-volume relationship. The sealed autoclave was heated to 210° C. for approximately twenty-four hours while stirring. These results are set forth in FIG. 4 and show that there was approximately a 55% conversion of ethylene to $C_6H_5CH_2CH_2CH_3$ isomer.

This experiment was repeated using propylene gas in place of ethylene gas with the sealed autoclave being heated to 180° C. (see FIG. 4). There was approximately a 40% conversion of propylene to a $C_6H_5CH_2$—$CH(CH_3)_2$ isomer.

EXAMPLE 6

Alkylation of Ethylene by Propylene

Figure 5:
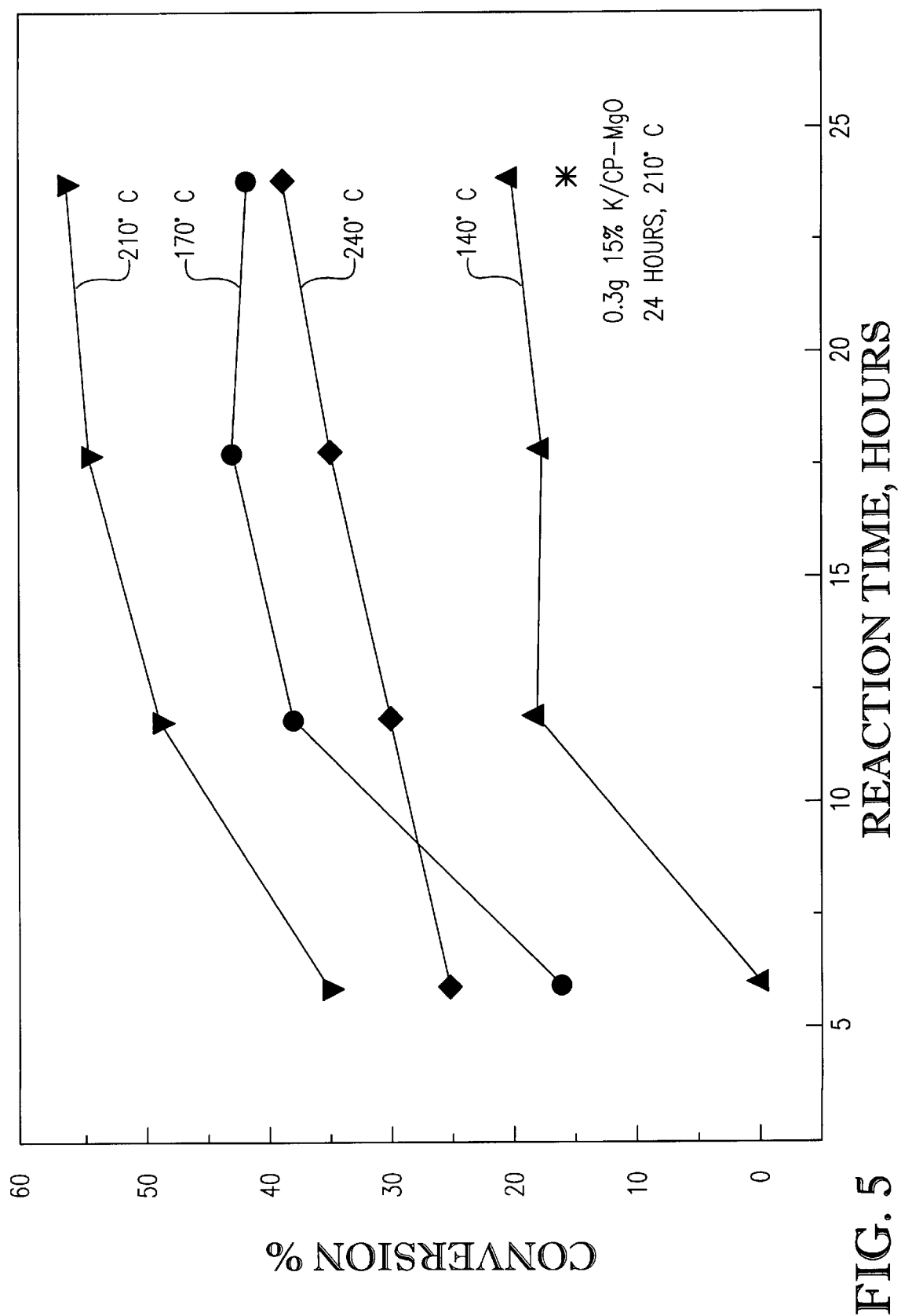
FIG. 5 is a graph depicting the alkylation of ethylene by propylene at various reaction temperatures.

This experiment was conducted to determine the effect of temperature on the ability of K/AP—MgO and propylene to alkylate ethylene. The procedures followed were as described in Part 3 of Example 2 with the exception that the sealed autoclave was heated to 140° C., 170° C., 210° C., or 240° C. The results of this experiment are set forth in FIG. 5 and indicate that, at a molar ratio of 1:1, conversion of propylene and ethylene to pentenes and heptenes took place at temperatures as low as 140° C. with maximum conversions occurring at 210° C. The percent conversion was only about 15% when utilizing K/CP—MgO at 210° C. compared to approximately 55% with K/AP—MgO at 210° C. These results provide further evidence of the importance of edge and corner sites in providing stronger superbases.

EXAMPLE 7

Characterization of Base Strength

The base strengths of various MgO samples (both with and without potassium loading) were determined by the Hammett-Deyrup H⁻function as described in Hammett, *Physical Organic Chemistry*, p. 269 (1940). The method is set forth in detail in Take et al., *J. Catal.*, 21:164 (1971), incorporated by reference herein. Briefly, an indicator was added to the sample and, if the sample changed the color of the indicator, the base strength of the sample was determined to be greater than or equal to the base strength of the indicator. The indicators used in this experiment were 2,4-dinitroaniline ($pK_{BH}$=15), 4-chloro-2-nitroaniline ($PK_{BH}$=17.2), aniline ($pK_{BH}$=27), and toluene ($PK_{BH}$=35).

The results are shown in Table I below and indicate that AP—MgO possesses a greater number of base sites and stronger base sites than CP—MgO. The 4 nm AP—MgO crystallites are approximately 30% surface. It has previously been determined that 20% of AP—MgO surface ions are on the corners or edges (Klabunde et al., *J. Phys. Chem.* 100:12142–12153 (1996)). Thus 6% (0.2×0.3) of all ions are on edges or corners corresponding to 1.5 mmol on edges/corners per gram of MgO. This value of 1.5 mmol is very close to the total base sites of 0.8 mmol/g on AP—MgO (see Table I).

Table I illustrates that, upon potassium doping of the MgO surface, base site concentrations increase and stronger sites are generated. Because AP—MgO and CP—MgO do not catalyze alkene isomerization or alkylation reactions absent potassium doping (see Examples 3 and 4), the base sites generated by potassium doping are responsible for the isomerization and alkylation reactions observed. Finally, the surface concentration of strongly basic sites corresponds to the difference in observed catalytic activity (i.e., K/AP—MgO exhibits greater catalytic activity than K/CP—MgO).

Figure 6:
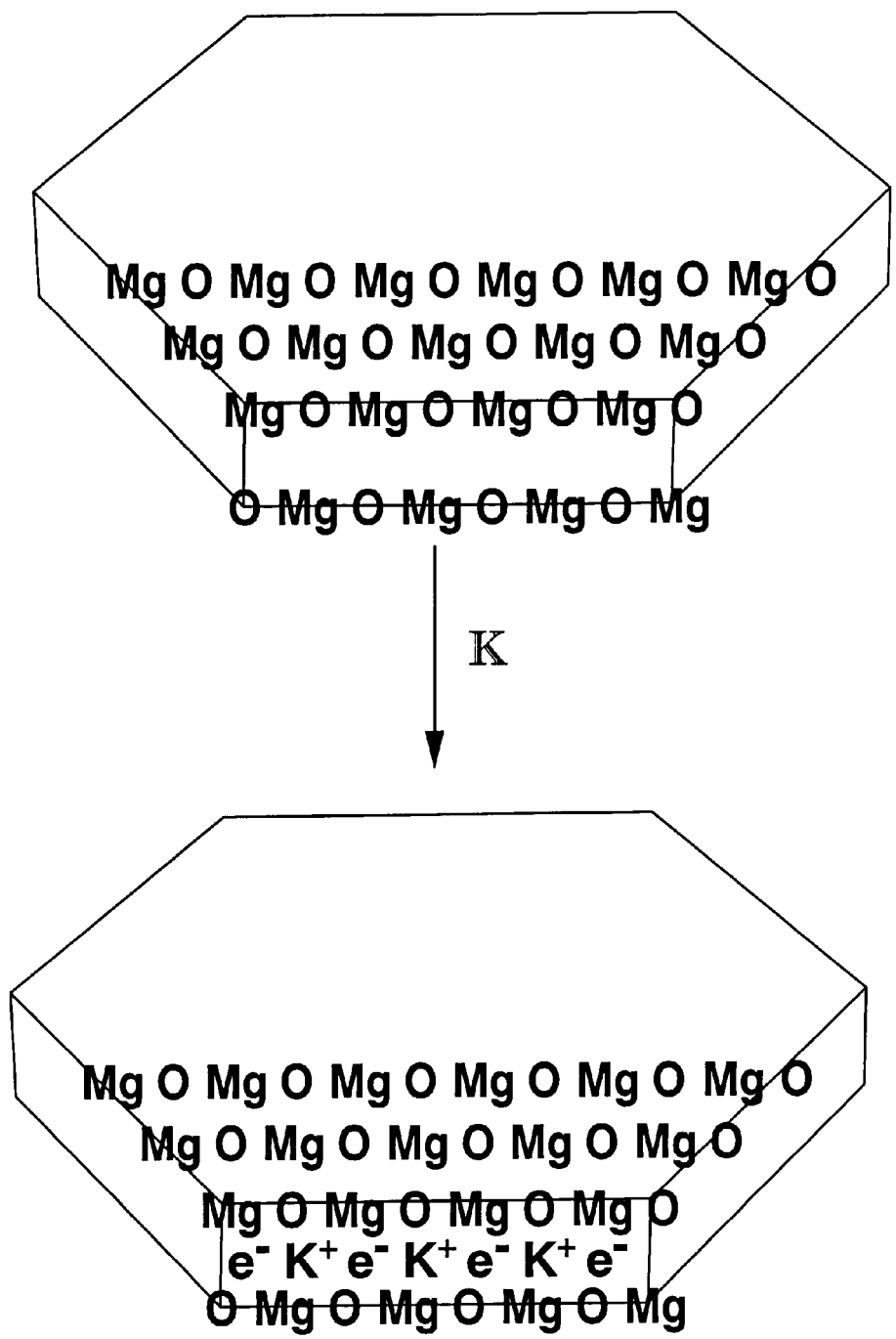
FIG. 6 illustrates the location of potassium atoms near the edge and corner sites on nanocrystalline CP—MgO.
Figure 7:
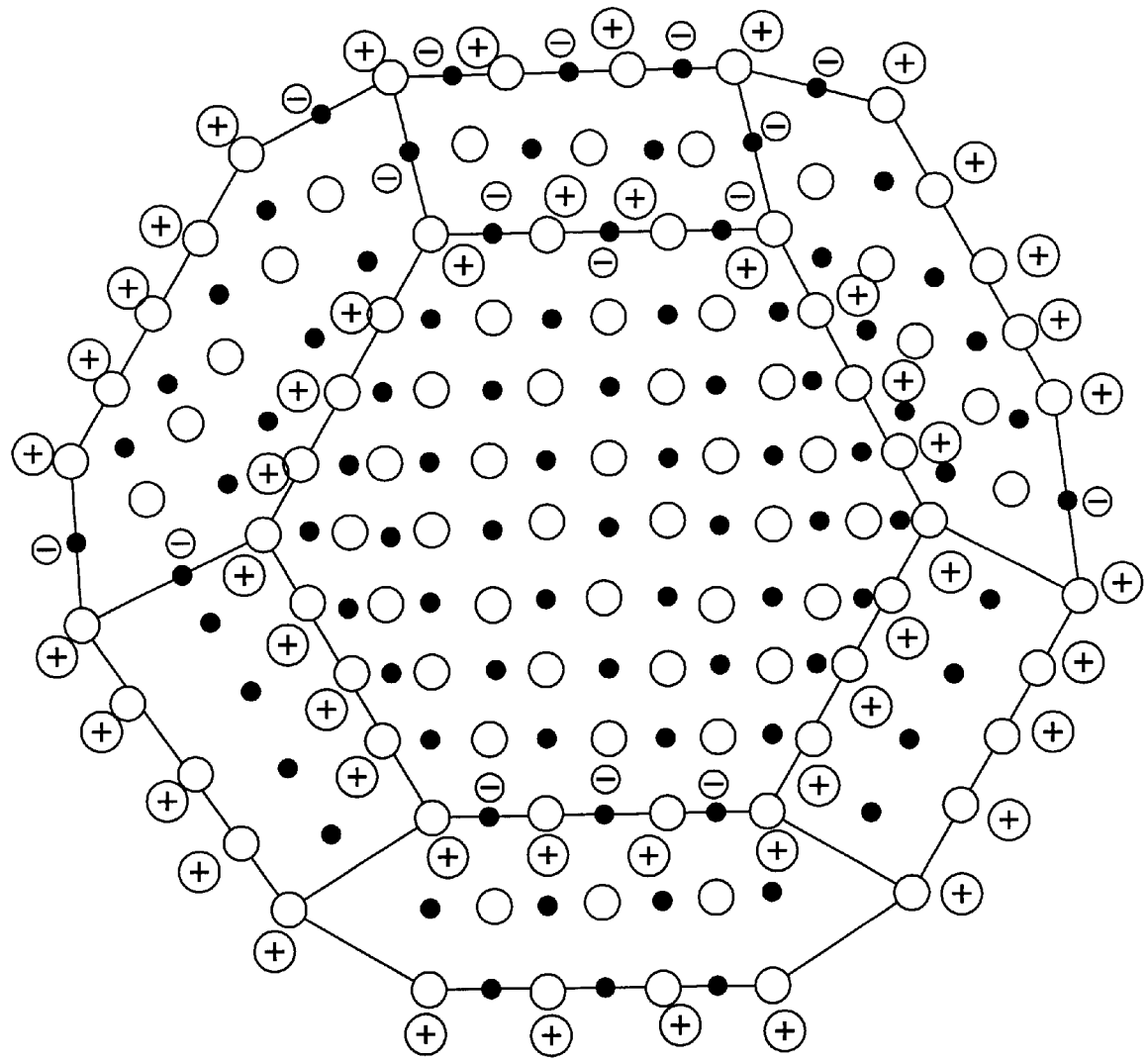
FIG. 7 shows an AP—MgO nanocrystal doped with potassium atoms that have dissociated into $K^+e^-$.

Comparing the base site strength of the 10% K/AP—MgO to the 15% K/AP—MgO from Table I, there is only a very slight increase in total base sites generated with an increase in potassium loading. Furthermore, the total base sites agree almost exactly with the calculated edge/corner sites (1.5 mmol per gram MgO). This provides further evidence that the edge/corner sites are responsible for stabilizing reactive molecules on metal oxides. This is the result of electrons trapped near edge/corner sites which enhance the basicity at the edge/corner sites. FIG. 6 and 7 illustrate potassium metal atoms congregated on the electron dense MgO edge/corner sites.

TABLE I

Base Strength of Various MgO Samples

| Samples | 15 to 17.2[b] | 17.2 to 27[b] | 27 to 35[b] | >35[b] | Total meq/g[c] |
|---|---|---|---|---|---|
| CP-MgO | 0 | 0.35 | 0 | 0 | 0.35 |
| AP-MgO | 0.2 | 0.4 | 0.2 | 0 | 0.8 |
| 10% K/Ap-MgO[a] | 0 | 0.9 | 0.5 | 0.15 | 1.55 |
| 15% K/Ap-MgO[a] | 0 | 0.95 | 0.45 | 0.2 | 1.6 |
| 10% K/CP-MgO[a] | 0.1 | 0.6 | 0.1 | 0 | 0.8 |

[a]Refers to percent loading of potassium on the MgO surface.
[b]A larger number indicates a weaker acid.
[c]Indicates total base sites.

Discussion of Superbase Sites

The superbase sites are formed when the reactive atoms (e.g. potassium) give up their electrons to Lewis acid sites in the vicinity of corner or edge $Mg^{2+}$ ions, thereby creating additional electron density at neighboring edge or corner $O^{2-}$ ions and causing the sites to become superbase sites. When potassium vapor is the metal source, each atom that adsorbs to the MgO surface dissociates into $K^+e^-$ in the initial stages. However, as more and more potassium is loaded onto the MgO surface, the surface becomes covered and the potassium begins to form a layer of potassium metal. The amount of potassium that dissociates depends upon the surface area and the number of Lewis acid base sites available. Higher surface area MgO can accept more potassium as $K^+e^-$ with the maximum possible loading of potassium as $K^+e^-$ being about 30–40% on AP—MgO and 10–20% on CP—MgO.

EXAMPLE 8

Halogenated Metal Oxides

The following procedures were followed to prepare halogenated metal oxides.

1. Chlorinated Metal Oxides

In order to prepare Cl/MgO or Cl/CaO, metal oxide samples (weighing from about 0.30 to about 1.0 g each) were placed in a Schlenk tube (340 ml vacuum tight glass tubes). Each sample tube was evacuated at room temperature and an excess of chlorine gas was allowed to enter the tube at a pressure of about 1 atm of chlorine. The amount of chlorine gas was determined to be an excess amount when the inlet gas remained green. The samples became hot to the touch when the chlorine entered the tubes, indicating that a reaction was taking place. The reaction was complete within one to two minutes, but each sample was allowed to stand for approximately 30 minutes before removal from the tube.

2. Brominated Metal Oxides

Br/MgO and Br/CaO were prepared in a manner similar to that described under Part 1. An excess of bromine gas was allowed to enter a Schlenk tube which contained from 0.30 to 1.0 g of the particular metal oxide sample at the vapor pressure of bromine at room temperature. The amount of bromine gas was determined to be an excess amount when the inlet gas remained dark red. The reaction was complete within several minutes, but each sample was allowed to stand for approximately 30 minutes before removal from the tube.

3. Iodinated Metal Oxides

I/MgO and I/CaO were prepared by placing 1.0 g of the metal oxide in a Schlenk tube along with 1.0 g of iodine. The air was evacuated from the tube, the stopcock was closed, and the mixture was heated to 90–100° C. The iodine vaporized and deposited onto the oxide particles. The sample was allowed to stand for about 30 minutes before removal from the sample tube.

EXAMPLE 9

Thermal Gravimetric Analysis (TGA)

The following experiments were conducted to determine the number of atoms of a halogen adsorbed on each square nanometer of surface of metal oxide. In each of these tests, the average weight loss of a halogenated metal oxide sample was determined and compared to the average weight loss of a non-halogenated metal oxide sample to determine the percent weight of the halogenated sample which was attributable to the halogen. This percent was used to derive the number of atoms of halogen adsorbed per square nanometer of metal oxide.

1. AP—MgO with Chlorine

Figure 8:
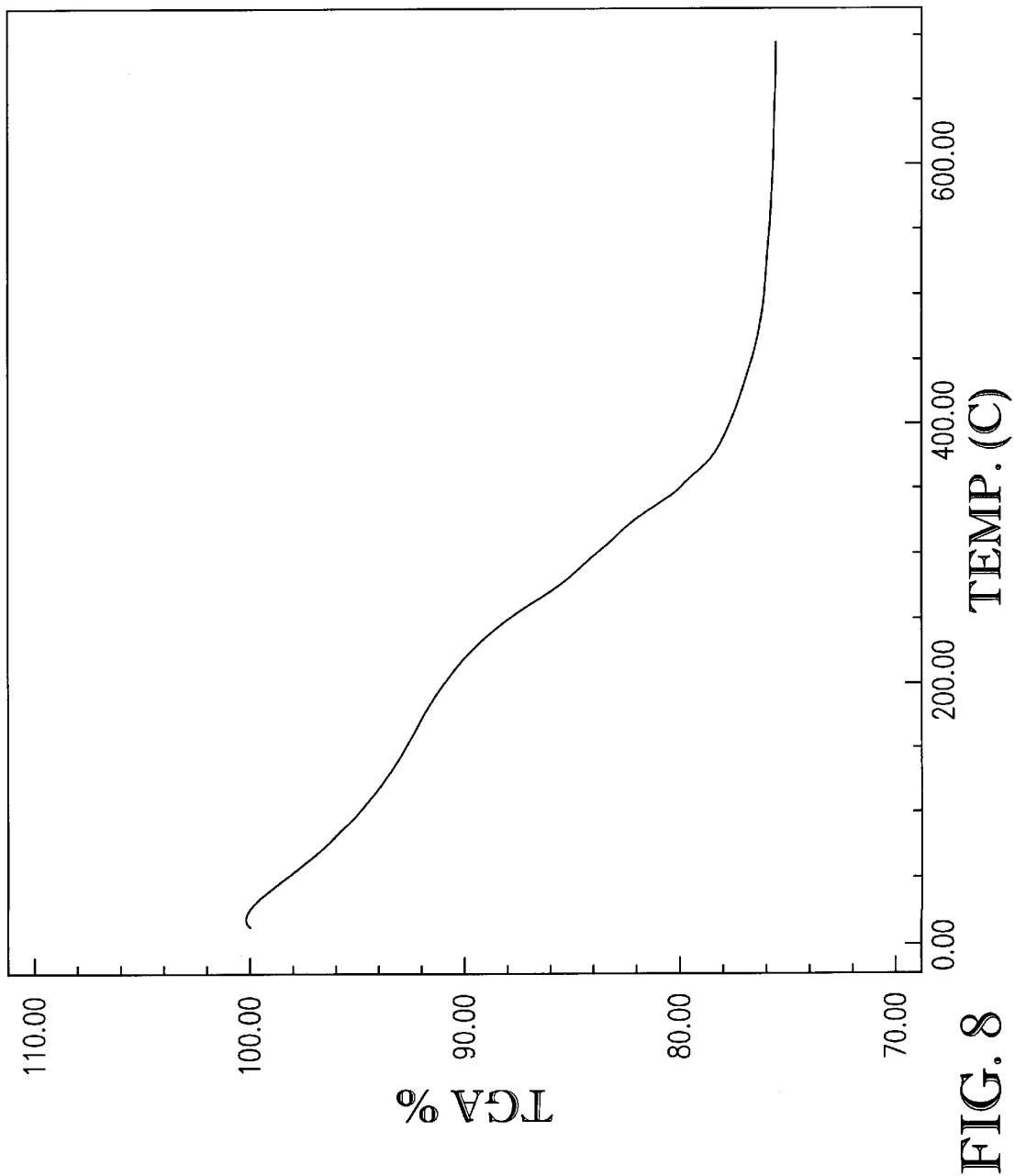
FIG. 8 is a graph showing the results of a thermogravimetric analysis of Cl/AP—MgO.

Approximately 1.0 g of AP—MgO was treated with excess chlorine gas following the procedure described in Part 1 of Example 8. The light yellow sample was transferred in air to a Shimadzu TGA apparatus (no color change occurred). The chamber was flushed with nitrogen and a TGA was carried out (i.e., the chlorinated metal oxide was heated to 700° C. at 10° C./min. with the weight of the mixture being measured continuously in order to determine the weight loss of each sample). This experiment was repeated several times with the results of one of these runs illustrated in FIG. 8.

The same TGA procedure was followed on a sample of non-chlorinated metal oxide. The average weight loss for AP—MgO and for Cl/AP—MgO while heating up to 700° C. was determine as follows:

| | |
|---|---|
| AP-MgO | 11.3 ± 0.5 average weight loss |
| Cl/AP-MgO | 24.2 ± 1 average weight loss |

Assuming that all the chlorine was desorbed at 700° C., and that there were x grams of chlorine per 1.0 gram of AP—MgO:

$$\frac{x}{(1.0\ \text{g} + x)} = (24.2\% - 11.3\%) \rightarrow x = 0.147\ \text{g Cl}_2 \text{ on } 1.0\ \text{g AP-MgO}$$

$$(0.147\ \text{g Cl}_2)\left(\frac{1\ \text{mole Cl}_2}{71\ \text{g}}\right)\left(\frac{1000\ \text{mmol}}{1\ \text{mole}}\right) = 2.08\ \text{mmol Cl}_2$$

$$(2.08\ \text{mmol Cl}_2)(2) = 4.16\ \text{mmol Cl}_2 \text{ atoms}$$

Surface area AP—MgO=430 nm$^2$/g
So, $$\left(\frac{4.16\ \text{mmol Cl atoms}}{1.0\ \text{g AP-MgO}}\right) \rightarrow$$

$$\frac{(4.16 \times 10^{-3}\ \text{mole/g})(6.02 \times 10^{23}\ \text{atoms/mole})}{430 \times 10^{18}\ \text{nm}^2/\text{g}} = 5.8\ \text{Cl atoms/nm}^2$$

Therefore, 5.8 Cl atoms were adsorbed per nm$^2$ of AP—MgO.

2. AP—MgO with Bromine

Figure 9:
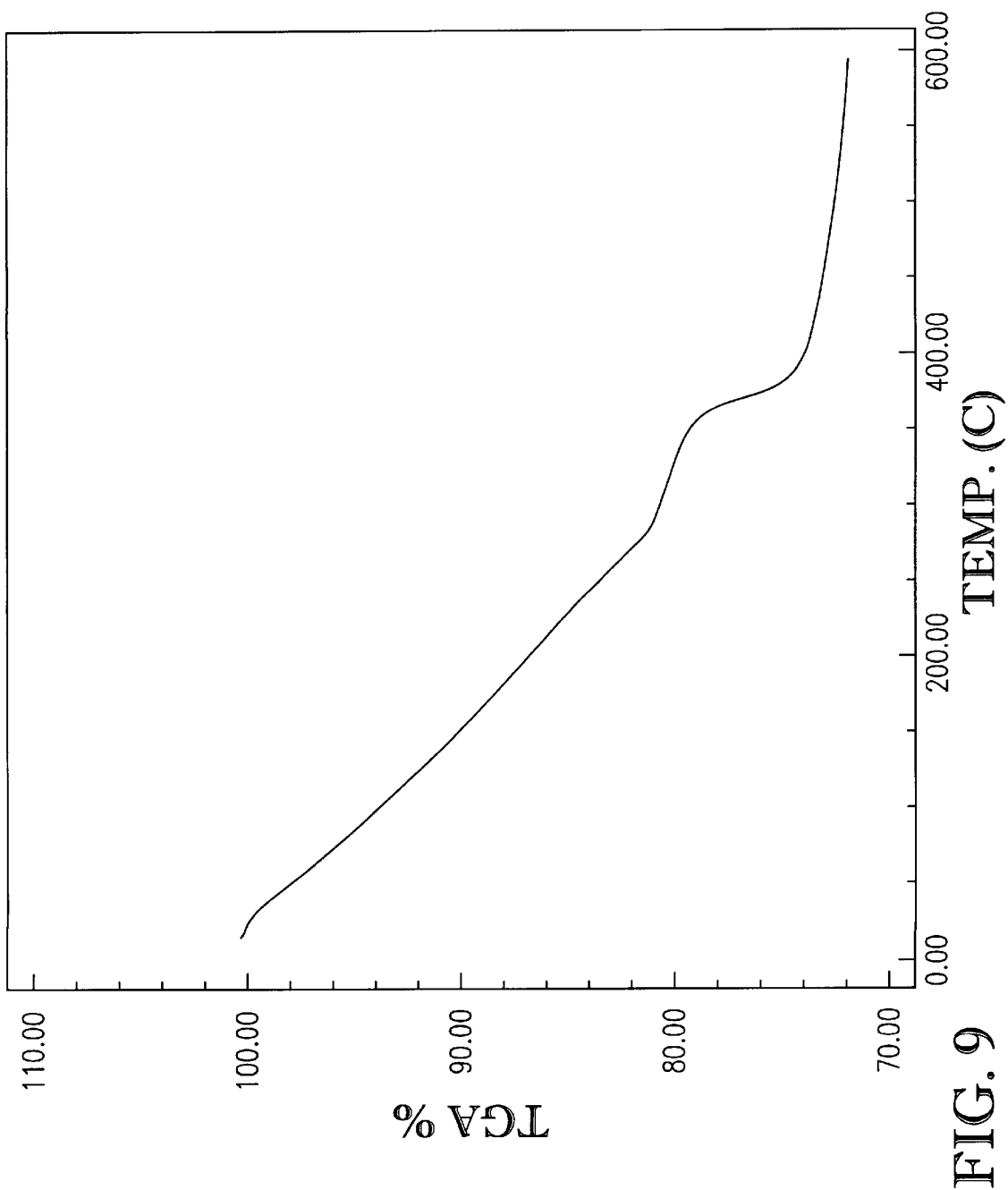
FIG. 9 is a graph setting forth the results of a thermogravimetric analysis of Br/AP—MgO.

An Ap—MgO sample (1.0 g) was treated with excess bromine as described in Part 2 of Example 8. The light brown colored sample was transferred in air to the TGA apparatus (no color change occurred). The chamber was flushed with nitrogen and a TGA was carried out. After four repetitions, the average weight loss of the sample was determined to be 13%. The results of one of these runs illustrated in FIG. 9. The number of Br atoms adsorbed on each square nanometer of AP—MgO was calculated in the same manner described under Part 1 of this example. Assuming that all the bromine was desorbed at 700° C., and that there were x grams of bromine per 1.0 gram of AP—MgO:

$$\frac{x}{1.0\ \text{g} + x} = 13\% \rightarrow x = .149\ \text{g Br}_2 \text{ on } 1.0\ \text{g AP-MgO}$$

$$(.149\ \text{g Br}_2)\left(\frac{1\ \text{mole Br}_2}{159.8\ \text{g}}\right)\left(\frac{1000\ \text{mmol}}{1\ \text{mole}}\right) = 0.932\ \text{mmol Br}_2$$

$$(0.932\ \text{mmol Br}_2)(2) = 1.864\ \text{mmol Br atoms}$$

Surface area AP—MgO=430 nm$^2$/g
So, $$\frac{1.864\ \text{mmol Br atoms}}{1.0\ \text{g AP-MgO}} \rightarrow$$

$$\frac{(1.864 \times 10^{-3}\ \text{mole/g})(6.02 \times 10^{23}\ \text{atoms/mole})}{430 \times 10^{18}\ \text{nm}^2/\text{g}} = 2.6\ \text{Br atoms/nm}^2$$

3. AP—MgO with Iodine

One gram of an AP—MgO sample was treated with 1 g of iodine following the procedure described in Part 3 of Example 8. The sample was transferred in air to the TGA apparatus (no color change occurred). The chamber was flushed with nitrogen and a TGA was carried out. This test was repeated several times and the average weight loss was determined to be 15%. The number of I atoms adsorbed on each square nanometer of AP—MgO was calculated in the same manner described under Part 1 of this example. Assuming that all of the iodine was desorbed at 700° C., and that there were x grams of iodine per 1.0 gram of AP—MgO:

$$\frac{x}{1.0 \text{ g} + x} = 15\% \rightarrow x = 0.176 \text{ g } I_2 \text{ on } 1.0 \text{ g AP-MgO}$$

$$(0.176 \text{ g } I_2)\left(\frac{1 \text{ mole } I_2}{253.8 \text{ g}}\right)\left(\frac{1000 \text{ mmol}}{1 \text{ mole}}\right) = 0.693 \text{ mmol } I_2$$

$$(0.693 \text{ mmol } I_2)(2) = 1.39 \text{ mmol I atoms}$$

Surface area AP—MgO=430 nm$^2$/g
So, $$\frac{1.39 \text{ mmol I atoms}}{1.0 \text{ g AP-MgO}} \rightarrow \frac{(1.39 \times 10^{-3} \text{ mole/g})(6.02 \times 10^{23} \text{ atoms/mole})}{430 \times 10^{18} \text{ nm}^2/\text{g}} =$$

$$2.0 \text{ I atoms/nm}^2$$

Therefore, 2.0 I atoms are adsorbed per nm$^2$ of AP—MgO.

EXAMPLE 10

Repeated Adsorption of Chlorine Atoms on AP—MgO

A series of readsorption experiments was carried out on the same metal oxide sample to determine if the adsorption-desorption of Cl$_2$ was reversible. The tests carried out were as follows:

(a) Chlorine was adsorbed onto AP—MgO following the procedure of Example 8. Then, following the procedures set forth in Part 1 of Example 9, the percent weight loss of the sample due to chlorine was determined to be 14%.

(b) The sample from step (a) was heated to 500° C. under vacuum for 4 hours.

(c) Step (a) was repeated on the sample from step (b) and the percent weight loss of the sample due to chlorine was determined to be 10%.

(d) The sample from step (c) was heated to 500° C. under vacuum for 4 hours.

(e) Step (a) was repeated on the sample from step (d) and the percent weight loss of the sample due to chlorine was determined to be 4.5%.

With each repetition of the adsorption and desorption, the percent weight loss of the sample decreased, indicating that chlorine adsorption on the metal oxide and chlorine desorption off the metal oxide are not completely reversible.

EXAMPLE 11

Absence of Chlorination of 2,3-dimethylbutane (DMBA) with Cl$_2$ (without AP—MgO or UV light)

Cl$_2$ (14 mmol) and DMBA (14 or 28 mmol) were allowed to mix in a glass Schlenk tube at room temperature in the dark. The sample was analyzed by gas chromatography. No peaks were observed in the chlorinated alkane region, thus indicating that no reaction took place.

EXAMPLE 12

Chlorination of DMBA with UV light

Cl$_2$ (14 mmol) and DMBA (14 or 28 mmol) were allowed to mix in a quartz photolysis tube and irradiated with unfiltered UV light (450 Watt lamp). The sample was analyzed by gas chromatography and indicated that a mixture of mono- and dichlorination products were formed.

EXAMPLE 13

Chlorination of DMBA in the presence of MgO or CaO samples without UV light.

Several experimental approaches were used to contact the chlorine, metal oxide and light.

(a) First, DMBA was added to a Schlenk tube containing AP—CaO. When Cl$_2$ was added to the sample tube, an explosive reaction was observed. The same result was found when this approach was repeated with CP—CaO.

(b) Cl$_2$ was added to a Schlenk tube containing AP—CaO. The heat of adsorption was allowed to dissipate until the sample was at room temperature at which time DMBA was introduced. DMBA chlorination products were formed, but no explosion occurred.

(c) Cl$_2$ was added to a Schlenk tube containing CP—CaO. The heat of adsorption was allowed to dissipate until the sample was at room temperature (25° C.) at which time DMBA was introduced. A violent explosion took place. This same result followed when DMBA was introduced to the sample at sample temperatures of 0° C. and −23° C. However, when DMBA was introduced to the Cl/CP—CaO sample at sample temperatures of −42° C. and −78° C., no explosion occurred. Instead, the reaction mixture slowly warmed to room temperature. Similar experiments were conducted with AP—MgO at sample temperatures of 25° C., 0° C., −42° C., and −78° C. Again, explosions occurred at 25° C. and 0° C., but at sample temperatures of −42° C. and −78° C., smooth chlorination of DMBA took place.

EXAMPLE 14

Determination of Selectivity of Chlorination Reactions

A series of experiments with CP—CaO, AP—CaO, and AP—MgO was carried out following the procedures described in Example 8. The DMBA was added to the chlorinated metal oxide samples at sample temperatures of −42° C. and −78° C., and the mixture was held at the low temperature (i.e., at either −42° C. or −78° C. for several hours). The volatile materials were removed under vacuum as the sample warmed to room temperature.

Analysis of the products by GC-MS showed the presence of a mixture of mono-, di-, and trichoro alkanes. It was found that the reaction temperature and ratio of Cl$_2$:DMBA affected the likelihood of forming the various products. The results are summarized in Table II. The reactivity order (most reactive to least reactive) was AP—MgO>CP—CaO>AP—CaO. Lower temperatures increased the selectivity of tertiary C—H bond chlorination, thus resulting in an increase in monochloroalkanes. These results are important because previously reaction temperatures of 200–300° C. or exposure of the reaction mixture to UV light was necessary in order to chlorinate alkanes.

TABLE II

The selectivity of chlorination reaction at different conditions

| Reaction Condition | Total Conversion % | Peak Area Ratios of t-Cl DMBA/p-Cl DMBA | Mono-chlorine DMBA % |
|---|---|---|---|
| DMBA & $Cl_2$ only, 1:1, UV for 1 hr | 95 | 1.2 | 44 |
| DMBA & $Cl_2$ only, 2:1, UV for 1 hr | 81 | 0.97 | 69 |
| DMBA & $Cl_2$, 2:1 CP-CaO, −42° C., 2 hr | 83 | 2.1 | 76 |
| DMBA & $Cl_2$m 2:1 CP-CaO, −78° C., 6 hr | 88 | 2.9 | 74 |
| DMBA & $Cl_2$, 3:1, CP-CaO, −78° C., 6 hr | 53 | 1.7 | 88 |
| DMBA & $Cl_2$, 2:1 AP-CaO, −78° C., 6 hr | 41 | 1.3 | 93 |
| DMBA & $Cl_2$, 3:1 AP-CaO, −78°, 6 hr | 22 | 1.3 | 94 |
| DMBA & $Cl_2$, 2:1 AP-MgO, −78° C., 6 hr | 96 | 1.8 | 35 |
| DMBA & $Cl_2$, 3:1, AP-MgO, −78° C., 6 hr | 78 | 1.6 | 75 |

EXAMPLE 15

Bromination of DMBA $Br_2$, DMBA, and CP—CaO were mixed in 1:1 molar ratios in the dark and at room temperature. After 24 hours the reaction mixture was checked for loss of the red-brown color due to $Br_2$ consumption. This same test was repeated with AP—MgO and AP—CaO. Qualitatively it was found that the presence of the oxides accelerated the reactions. The reactions proceeded in the following order (from fastest to slowest) thus indicating the ability of each metal oxide to take up bromine: CP—CaO>AP—MgO>AP—CaO>no oxide present.

EXAMPLE 16

Iodination of DMBA with $I_2$

Iodination of DMBA was attempted in a series of experiments. The following mixtures were tested: $I_2$+DMBA+UV light; $I_2$+DMBA+AP—CaO (both with and without UV light); $I_2$+DMBA+CP—CaO (both with and without UV light); and, $I_2$+DMBA+AP—MgO (both with and without UV light). No iodination reactions took place in any of the experiments.

We claim:

1. A composition comprising a metal oxide particle with a number of atoms stabilized on the surface thereof, said atoms selected from the group consisting of the halogens and Group IA metals and being present at a level of at least about 2 atoms per square nanometer of metal oxide surface area.

2. The composition of claim 1, said particle having an average crystallite size of up to about 20 nm.

3. The composition of claim 2, said average crystallite size being about 3–6 nm.

4. The composition of claim 3, said average crystallite size being about 4 nm.

5. The composition of claim 1, said particle having a multi-point surface area of at least about 15 $m^2/g$.

6. The composition of claim 5, said surface area being at least about 200 $m^2/g$.

7. The composition of claim 6, said surface area being at least about 500 $m^2/g$.

8. The composition of claim 1, said particle being selected from the group consisting of MgO, CaO, $TiO_2$, $ZrO_2$, FeO, $V_2O_3$, $V_2O_5$, $Mn_2O_3$, $Fe_2O_3$, NiO, CuO $Al_2O_3$, ZnO, and mixtures thereof.

9. The composition of claim 8, said particle being MgO.

10. The composition of claim 8, said particle being CaO.

11. The composition of claim 1, said atom being a chlorine atom.

12. The composition of claim 1, said level being about 3–8 atoms per square nanometer of metal oxide surface area.

13. The composition of claim 11, wherein the composition has a surface hydroxyl concentration of less than about 5 hydroxyl groups per square nanometer of metal oxide surface area.

14. A method of forming a metal ion/reactive atom composition comprising the steps of:
    (a) providing a quantity of metal oxide particles;
    (b) contacting said particles with a source of reactive atoms selected from the group consisting of halogen and Group IA metal atoms under conditions to attach said atoms to the surfaces of said particles at a level of at least about 2 atoms per square nanometer of metal oxide particle surface area.

15. The method of claim 14, further including the steps of heating said metal oxide particles to a temperature of at least about 200° C. prior to step (b).

16. The method of claim of claim 14, wherein said particles are selected from the group consisting of MgO, CaO, $TiO_2$, $ZrO_2$, FeO, $V_2O_3$, $V_2O_5$, $Mn_2O_3$, $Fe_2O_3$NiO, CuO, $Al_2O_3$, ZnO, and mixtures thereof.

17. The method of claim 16, wherein said particle is MgO.

18. The method of claim 16, wherein said particle is CaO.

19. The method of claim 14, wherein said atoms are halogens.

20. The method of claim 19, wherein said atoms are chlorine atoms.

21. The method of claim 14, said particle having a multi-point surface area of at least about 15 $m^2/g$.

22. The method of claim 21, said surface area being at least about 200 $m^2/g$.

23. The method of claim 22, said surface area being at least about 500 $m^2/g$.

24. The method of claim 14, said source of reactive atoms comprising a compound which under said conditions dissociates to generate said reactive atoms.

25. The method of claim 14, said particles having an average crystallite size of up to about 20 nm.

26. The method of claim 25, said particles having an average crystallite size of from about 3–6 nm.

27. The method of claim 26, said average crystallite size being about 4 nm.

28. The method of claim 15, further including the step of cooling said particles to a temperature of from about −20 to about 25° C. after said heating step.

29. The method of claim 20, wherein the product of step (b) has a total surface hydroxyl group concentration of less than about 5 hydroxyl groups per square nanometer of metal oxide surface area.

30. A composite comprising a self-sustaining body formed of a plurality of agglomerated metal oxide particles with a number of atoms stabilized on the surface thereof, said atoms selected from the group consisting of the halogens and Group IA metals and said atoms being present at a level at least about 2 atoms per square nanometer of metal oxide surface area.

31. The composite of claim 30, said particles being selected from the group consisting of MgO, CaO, $TiO_2$, $ZrO_2$, FeO, $V_2O_3$, $V_2O_5$, $Mn_2O_3$, $Fe_2O_3$, NiO, CuO, $Al_2O_3$, ZnO, and mixtures thereof.

32. The composite of claim 31, said particles being MgO.

33. The composite of claim 31, said particles being CaO.

34. The composite of claim 30, said particles having surface-stabilized atoms being pressed at a pressure of from about 50 psi to about 6,000 psi.

35. The composite of claim 34, said particles having surface-stabilized atoms being pressed at a pressure of from about 500 psi to about 5,000 psi.

36. The composite of claim 35, said particles having surface-stabilized atoms being pressed at a pressure of about 2,000 psi.

37. The composite of claim 30, wherein said particles having surface-stabilized atoms are pressed-together.

38. A composition comprising a metal oxide particle with a number of atoms stabilized on the surface thereof forming a metal oxide-atom adduct, wherein said atoms are selected from the group consisting of the halogens and Group IA metals, and wherein when said adduct is heated to a temperature of about 100° C. less than about 10% of the total weight loss of the adduct is attributable to the desorption of said atoms.

39. The composition of claim 38, said atoms being present at a level of at least about 2 atoms per square nanometer of metal oxide surface area.

40. The composition of claim 39, said level being from about 2 to 14 atoms per square nanometer of metal oxide surface area.

41. The composition of claim 38, said particle having an average crystallite size of up to about 20 nm.

42. The composition of claim 41, said average crystallite size being about 3–6 nm.

43. The composition of claim 42, said average crystallite size being about 4 nm.

44. The composition of claim 38, said particle having a multi-point surface area of at least about 15 $m^2/g$.

45. The composition of claim 44, said surface area being at least about 200 $m^2/g$.

46. The composition of claim 45, said surface area being at least about 500 $m^2/g$.

47. The composition of claim 38, said particle being selected from the group consisting of MgO, CaO, $TiO_2$, $ZrO_2$, FeO, $V_2O_3$, $V_2O_5$, $Mn_2O_3$, $Fe_2O_3$, NiO, CuO, $Al_2O_3$, ZnO, and mixtures thereof.

48. The composition of claim 47, said particle being MgO.

49. The composition of claim 47, said particle being CaO.

50. The composition of claim 38, said atom being a chlorine atom.

51. The composition of claim 50, wherein said composition has a surface hydroxyl concentration of less than about 5 surface hydroxyl groups per square nanometer of metal oxide surface area.

* * * * *

UNITED STATES PATENT AND TRADEMARK OFFICE
CERTIFICATE OF CORRECTION

PATENT NO. : 6,087,294
DATED : July 11, 2000
INVENTOR(S) : Kenneth J. Klabunde et al.

It is certified that error appears in the above-identified patent and that said Letters Patent is hereby corrected as shown below:

Column 1,
Line 4, please insert the following paragraph:
  -- FEDERALLY SPONSORED RESEARCH/DEVELOPMENT PROGRAM
     This invention was made with government support under Grant DAAG96-1-0166 awarded by the United States Army Research Office. The government has certain rights in this invention. --

Signed and Sealed this

Thirtieth Day of April, 2002

Attest:

Attesting Officer

JAMES E. ROGAN
Director of the United States Patent and Trademark Office